United States Patent [19]

Shah et al.

[11] Patent Number: 5,558,989
[45] Date of Patent: Sep. 24, 1996

[54] **NUCLEIC ACID PROBES FOR THE DETECTION OF *GIARDIA LAMBLIA***

[75] Inventors: Jyotsna S. Shah, Nashua, N.H.; Amelia Buharin, Roslindale; David J. Lane, Milford, both of Mass.

[73] Assignee: Amoco Corporation

[21] Appl. No.: 239,949

[22] Filed: May 9, 1994

Related U.S. Application Data

[63] Continuation of Ser. No. 123,862, Sep. 20, 1993, abandoned, which is a continuation of Ser. No. 877,256, Apr. 28, 1992, abandoned, which is a continuation of Ser. No. 510,476, Apr. 18, 1990, abandoned.

[51] Int. Cl.$^6$ .................. C12Q 1/68; C07H 21/02; C07H 21/04
[52] U.S. Cl. .................. 435/6; 536/23.1; 536/24.3; 536/24.33
[58] Field of Search .................. 435/6; 536/23.1, 536/24.3, 24.33

[56] References Cited

U.S. PATENT DOCUMENTS

| | | | |
|---|---|---|---|
| 4,563,419 | 1/1986 | Ranki et al. | 435/6 |
| 4,717,653 | 1/1988 | Webster | 435/5 |
| 4,851,330 | 7/1989 | Kohne | 435/6 |

FOREIGN PATENT DOCUMENTS

| | | | |
|---|---|---|---|
| 0831459 | 9/1982 | European Pat. Off. | |
| 0130515 | 6/1984 | European Pat. Off. | 435/6 |
| WO88/03957 | of 1988 | European Pat. Off. | |
| 2169403 | 7/1986 | United Kingdom . | |
| WO84/02721 | 7/1984 | WIPO . | |
| WO84/03520 | 9/1984 | WIPO . | |

OTHER PUBLICATIONS

Sogin, M. L., et al., *Science*, 243: 75–77 (1989).
Pace, B. and Campbell, L. L., *J. of Bacteriology*, 107(2): 543–547 (1971).
Kohne, D. E., *Biophysical J.*, 8: 1104–1118 (1968).
Edlind, T. D. and Chakraborty, P. R., *Nucleic Acids Research*, 15(19): 7889–7901 (1987).
Boothroyd, J. C., et al., Nucleic Acids Research, 15(10): 4065–4084 (1987).
Abbaszadegan et al. (1991), *Detection of Giardia cysts with a cDNA probe and applications to water samples*, 57 Appl. Environ. Microbiol. (No. 4) 927–931.
Segrance Search Printout, Nov. 4, 1994, pp. 1–10.
Barry et al. Biotech 8:233 (1990).
Healey et al. Nucl. Acid Res. 18(13) 4006 (1990).
F.E.B.S. V. 183 (2) 379–82 (1985).
Biochem. Soc. Trans. 17:363–4 (1988).
Nucleic Acid Res. 15(10) 4065–84 (1987).
Science V. 243: 75–77 (1989).

*Primary Examiner*—Margaret Parr
*Assistant Examiner*—Paul B. Tran
*Attorney, Agent, or Firm*—Norval B. Galloway

[57] ABSTRACT

The present invention relates to a method of selectively detecting *Giardia lamblia* in a sample. The method makes use of at least one nucleic acid probe which is a DNA or PNA sequence which hybridizes, under appropriate conditions, to the ribosomal RNA or the ribosomal DNA of *Giardia lamblia* but does not hybridize to the ribosomal RNA or the ribosomal DNA of other organisms (non-*Giardia lamblia* organisms) which may be present in a sample.

14 Claims, 3 Drawing Sheets

```
Pos. #              124              141          152
                     |                |            |
P1446          3'CCAACGTGGGGGGCGCCGCCAGGGACGATCGGCCTGTG-5'              P1446
P1673                           3'GGACGATCGGCCTGTGGCGACCG-TTGGGCG       P1673
G.lamblia      GGACAACGGUUGCACCCCCCGCGGCGGUCCCUGCUAGCCGGACACCGCUGGC-AACCCGG  G.lamblia
E. coli        GUAAUGUCUGGG-----AAACUGCCUGAUGG----AGGGGGAUAACUACUGGAAA-CGGU  E. coli Pos. #                           185 188                                 188
                                  |   |                                   |
P1673          GCGGTTCTGCACGCG-CGT-5'                                     P1673
P1449                        3'CGCCCGCGGGCGCCCGCTCGTCGCACTGCGTCGCTGCCGGG-5'  P1449
G.lamblia      CGCCAAGACGUGCGC-GCAAGGGCGGGCGCCCGCGGGCGAGCAGCGUGACGCAGCGACGGCCCGCCC  G.lamblia
E. coli        AGCUAAUACCGCAUAACGUCGC---------------------------------------  E. coli Pos: #                           244                              283
                                  |                                |
495    3 P1448          3'AGTGGGCCAGCCGCGCCAGCGCCGCGCGGCTCCCGGGCTG-5'     P1448
495    8 G.lamblia  CGGGGCAUCACCCGGUCGGCGCGGUCGCGGCGCGCCGAGGGCCCGACGCCUGGCGG         G.lamblia
495    9 E. coli   GAUGGGAUUAGCUAGUAGGUGGGGUAACGGCUCACCUAGGCGACGAUCCCU-AGCU          E. coli Pos: #                      409
                             |
722    6 P1672          3'GCGCG---------------CTCGC------TCCGCCCGGGT----------  P1672
722    8 G.lamblia     -----AGCGCGC---------------GAGCG------AGGCGGGCCCA----------  G.lamblia
722    9 E. coli       GCGUGUAUGAAGAAGGCCUUCGGGUUGUAAAGUACUUUCAGCGGGGAGGAAGGGAGUAAA  E. coli Pos: #                                         500
                                                |
784    6 P1672         -------------------GTCGGGCGCGGCGCC---TC-5'    P1672
784    8 G.lamblia     -------------------CAGCCCCCGCCGCGC---AGCCGAGGGCA  G.lamblia
784    9 E. coli       GUUAAUACCUUUGCUCAUUGACGUUACCCGCAGAAGAA-GCACCGGCUA  E. coli
```

FIGURE 1A

```
Pos. #              124                  141           152
                     |                    |             |
P1446                                     3'CCAACGUGGGGGCGCCCCAGGACGAUCGGCCUGUG-5'
P1673                                      3'GGACGAUCGGCCUGUGGCGACCG-UUGGCG
G.lamblia    GGACAACGGUUGCACCCCCGGGCGGUCCCUGCCUAGCCGGACACCGCCUGGC-AACCCGG
E. coli      GUAAUGUCUGG------AAACUGCCUGAUGG------AGGGGAUAAACUACUGGAAA-CGGU Pos. #               185 188                                188
                      |   |                                  |
P1673        GCGGUUCUCUGCACGCG-CGU-5'
P1449                          3'CGCCCCGGGGCGCCCCGCUCGUCGCACUGCCUGCUGCCGGG-5'
G.lamblia    CGCCAAGACGUGCGC-GCAAGGGCGGGGCGCCCCGGGCGGGAGCAGCGUGACGCAGCGGCCCGCCC
E. coli      AGCUAAAUACCGCAUAACGUCGC- Pos:#              244                                           283
                    |                                             |
                    3'AGUGGGCCAGCCGCGCCGGCCAGCCGCCUCCCGGGCUG-5'            P1448
495  3 P1448
495  8 G.lamblia   CGGGCAUCACCCGGUCGCGGUAGGCCCGAGGCCCGACGCCUGGCGG          G.lamblia
495  9 E. coli    GAUGGGAUUAGCUAGUAAGGUGGGUAACGGCUCACCUAGCCGACGAUCCCU-AGCU       E. coli Pos: #             409
                    |
                    3'GCGCG-------------CUCGC-------TCCGCCCGGGU-----      P1672
722  6 P1672
722  8 G.lamblia   ------AGCGCGC------------GAGCG------AGGCGGGCCCA------        G.lamblia
722  9 E. coli    GCGUGUAUGAAGAAGCCCUUCGGGUUGUAAAGUACUUUCAGCGGGAGGAAGGAGUAAA     E. coli Pos: #                                          500
                                                 |
                    --------------GUCGGGCGCGGCGCC----TC-5'               P1672
784  6 P1672
784  8 G.lamblia   ------------CAGCCCCCGCCGGG---AGCCGAGGGCA                   G.lamblia
784  9 E. coli    GUUAAUACCUUGCUCAUUGACGUUACCCCCAGAAGAA-GCACCGGCUA             E. coli
```

FIGURE 1B

```
Pos: #              596
P1450           3'GGC------------------------------------------------GGTGC   P1450
G.lamblia       CCCCGCCG-------------------CCACG---------                    G.lamblia
E. coli         UGUU-AAGUCAGAUGUGAAAUCCCGGGCUCAACCUGGAACUGCAUCUGAUACUGGCAAGCU-- E. coli Pos: #                    652     652
P1450                      --      --                                       P1450
P1674                                3'CGGGGCAACCT-GGGGCGGCGACCCTGGCGCTCGCCCGCGTCGCCCCGCGCGG-5'  P1674
P1450                     TCCTTTGCCCTCGCGGAGGTCCGTCCGGGCAAC-5'
G.lamblia       AGGAAACGGGAGCGCUCCAGGA-CCCGCCGCGCGUUGGA-CCCGCCGCAGGCCUCCAGGACCGCGCCGCGUGGGACCGCGCGGGGACCGCGCCGGC  G.lamblia
E. coli         ----------------------------------------------------------------------------------------------   E. coli
```

NUCLEIC ACID PROBES FOR THE DETECTION OF *GIARDIA LAMBLIA*

This application is a continuation of application Ser. No. 08/123,862, filed Sep. 20, 1993, now abandoned, which is a continuation of application Ser. No. 07/877,256, filed Apr. 28, 1992, now abandoned, which is a continuation of application Ser. No. 07/510,476, filed Apr. 18, 1990, now abandoned.

BACKGROUND OF THE INVENTION

*Giardia lamblia* is a flagellated protozoan parasite which is a common cause of diarrhea in many countries throughout the world. Its life cycle consists of two stages, the trophozoite and the cyst. The trophozoite replicates in the small intestine and can cause disease in the susceptible host. Trophozoites are not usually found except in liquid stools of patients with diarrhea or upon purgation. When present, they exhibit motility that resembles Brownian motion in water. When a purgative is used, some trophozoites become inactive. They can encyst in the small intestine and are excreted in the feces. Other hosts are subsequently infected by ingestion of these cysts.

*Giardia lamblia* produces giardiasis and lives high in the intestinal tract. Considerable clinical evidence suggests that the trophozoites may be capable of producing inflammatory changes in the itestinal wall. Trophozoites of this parasite may be recovered in duodenal drainage or from the gall bladder. Proof of its primary role in gastrointestinal disease is available (Hoskins, L. C., et al., *Gastroenterology*, 53: 265–268 (1967); *Morbidity and Mortality*, Weekly Report, Center for Disease Control 19 (47): 455–459 (1970)).

The most commonly used method for diagnosing giardiasis is the identification of *Giardia lamblia* cysts or trophozoites in stools by histological staining techniques using Lugol's solution, merthiodate-iodine-formaldehyde or trichrome. These methods are time consuming, tedious and insensitive. A number of rapid laboratory methods have become available. A detection method with increased specificity would be valuable to clinicians because it would make it possible to differentiate *Giardia lamblia* from other organisms present in a sample being analyzed.

SUMMARY OF THE INVENTIONS

The present invention relates to a method of selectively detecting *Giardia lamblia* in a sample in which *Giardia lamblia* is suspected to be present. That is, it is a method by which *Giardia lamblia* present in a sample can be identified, to the exclusion of other organisms (referred to as non-*Giardia lamblia* organisms) in the sample.

In particular, the invention relates to a method which makes use of at least one nucleic acid probe which is a DNA or RNA sequence which hybridizes, under appropriate conditions, to the ribosomal RNA or the ribosomal DNA of *Giardia lamblia*, but which does not hybridize, under the same conditions, to the ribosomal RNA or ribosomal DNA of other organisms (non-*Giardia lamblia* organisms) which may be present in a sample.

The present invention is particularly useful because it has the following advantages over presently available methods: 1) increased specificity for detecting *Giardia lamblia* in a sample; 2) accurate identification of biochemically unusual strains of *Giardia lamblia*; and 3) faster results because such tests do not require the isolation of *Giardia lamblia* from the sample prior to testing.

BRIEF DESCRIPTION OF THE DRAWINGS

FIG. 1 is a schematic representation of the alignment of the nucleotide sequences of the preferred 18S ribosomal RNA targeted probes of the present invention aligned upon their *Giardia lamblia* target nucleotide sequences. The corresponding portion of the 16S ribosomal RNA from *E. coli* is shown for comparison. RNA (target) sequences are written 5' to 3' and probe sequences are DNA and written 3' to 5'.

DETAILED DESCRIPTION OF THE INVENTION

Figure 2:
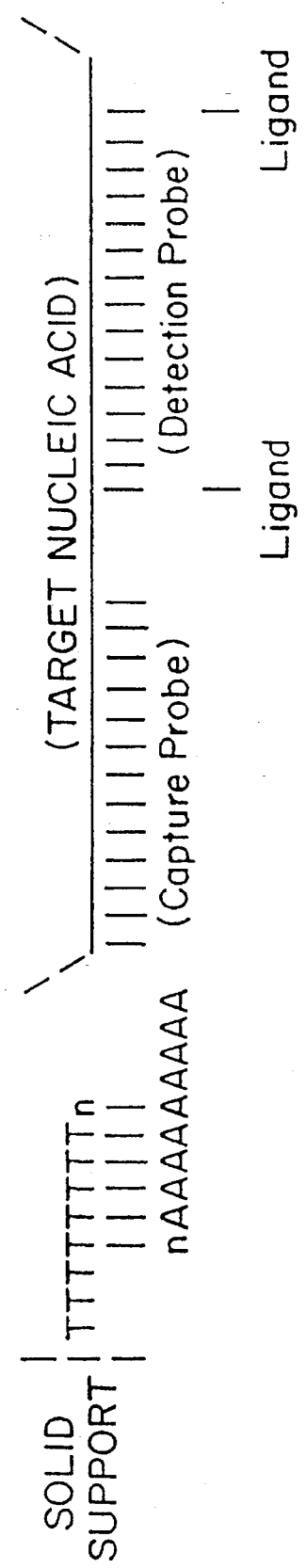
FIG. 2 is a schematic illustration of a hybridization complex comprised of a solid support, a capture probe, a target nucleotide sequence and a detection probe.

The present invention is a method of selectively detecting *Giardia lamblia* in a sample, through the use of at least one nucleic acid probe which hybridizes to at least a region of ribosomal RNA of *Giardia lamblia* or to at least a region of ribosomal DNA of *Giardia lamblia* (i.e., a target nucleotide sequence), but which does not hybridize to ribosomal RNA or ribosomal DNA of other organisms (i.e., non-*Giardia lamblia* organisms).

Briefly, the present method includes the following steps: 1) obtaining a sample to be analyzed; 2) treating the sample to render nucleic acids present available for hybridization with complementary nucleotide sequences; 3) combining the treated sample and at least one selected nucleic acid probe (i.e., at least one nucleic acid which hybridizes to at least a region of ribosomal RNA of *Giardia lamblia* or to at least a region of ribosomal DNA of *Giardia lamblia*), under appropriate conditions for hybridization of complementary sequences; and 4) detecting hybridization of the selected nucleic acid probes with nucleic acids present in the treated sample, which is indicative of the presence of *Giardia lamblia*.

The present method can be used on any sample in which *Giardia lamblia* is suspected to be present and which is sufficiently liquid to allow contact of nucleic acid sequences present in the sample with a nucleic acid probe and hybridization of complementary sequences to occur. The sample can be a clinical sample, such as feces and fecal samples from the lower intestine or an environmental sample, such as water. In addition, this method can be used to detect *Giardia lamblia* on filtering devices now commonly used to purify water.

The sample is treated in such a manner that the nucleic acids present in the sample are available for hybridization with a complementary nucleic acid sequence. For example, a sample can be treated with an agent which disrupts the cellular and molecular structures of the organism. Cells, such as protozoan parasites, can be disrupted, using chaotropic agents which disrupt the molecular structure of the organism. That is, the agent denatures the secondary, tertiary and/or quarternary structures of biopolymers, including proteins, nucleic acids, polysaccharides which are generally found in biological specimens. Examples of chaotropic agents include chaotropic salts (e.g., guanidinium thiocyanate), hydrolytic enzymes (e.g., proteases) and compounds that disrupt hydrophobic interrractions (e.g., sodium dodecyl sulfate, phenols, dimethylformamide, dimethylsulfoxide, tetramethylurea, or guanidinium hydrochloride). Physical or mechanical means of disrupting molecular structures (e.g., bead beating and sonication) can also be used to release nucleic acids. If necessary, nucleic acids present in the protozoan parasites and released from them can be treated further to ensure that they are available for hybridization with complementary nucleic acid sequences (e.g., by heating to render double stranded sequences single stranded). Agents and techniques that disrupt molecular structures can be used singly or in various combinations for this purpose.

After the nucleic acids are rendered available for hybridization, the sample is combined with a nucleic acid probe which hybridizes selectively with ribosomal RNA and/or ribosomal DNA of *Giardia lamblia*, or with a set (two or more) of such probes. Such nucleic acid probes (referred to as selected nucleic acid probes) are sufficiently complementary in sequence to ribosomal RNA and/or ribosomal DNA of *Giardia lamblia* that they hybridize to the *Giardia lamblia* ribosomal RNA or DNA, but not to nucleic acids present in other organisms (referred to as non-*Giardia lamblia* organisms). In certain possible assay formats only one of the probes need be specific for *Giardia lamblia*. In general, such probes are sufficiently long to hybridize and remain hybridized under the assay conditions. The appropriate length will be determined by the format used.

In the present method, the sample, treated as described above, is combined with a selected nucleic acid probe(s). In one embodiment of the present method, two types of *Giardia lamblia*-specific nucleic acid probes are contacted with the sample, either simultaneously or sequentially: *Giardia lamblia*-specific tailed capture probes and labelled detector probes.

One type of probe is a *Giardia lamblia*-specific tailed capture probe, which can be free or hybridized to a solid support. Tailed capture probes serve two purposes: they are complementary to (hybridize to) at least a portion of the 18S ribosomal RNA or 18S ribosomal DNA of *Giardia lamblia*, and they link the hybridization complexes, (described below) to a solid support, thus making it possible to separate the hybridization complex from the remainder of the sample.

The capture probes are characterized by a polynucleotide tail which is generally formed from a nucleotide homopolymer, such as polydoxyriboadenylate (poly (dA)), polydeoxyribocytidylate (poly (dC)), polydeoxyriboguanylate (poly(dG)) or polydeoxyribothymidylate (poly (dT)). The probe tail is complementary to a polynucleotide sequence which is affixed to a solid support, such as magnetic beads, polystyrene beads and polystyrene dipsticks, allowing the probe to be captured and separated from the sample.

Labelled detector probes are nucleic acid sequences which include a detectable label and are generally single-stranded RNA or DNA probes which hybridize to at least a portion of the 18S ribosomal RNA or a portion of the 18S ribosomal DNA of *Giardia lamblia*. Probes can be labelled isotopically (radioactivity) or non-isotopically. A particularly useful label is one which is detectable at low levels, is stable, does not interfere with the hybridization reaction and has low background. Radioactive isotopes such as phosphorus 32, sulfur 35 and iodine 125, can be used. Examples of non-isotopic labels which can be used are enzyme labelled antibodies and acridium esters. Oligonucleotide probes containing a modified cytotidine are labelled with fluorescein. These fluorescenated probes are detected in their target complexes by the use of anti-fluorescein antibodies that have been labelled with an enzyme. The use of acridium ester labels allows for very sensitive detection of nucleotides and detection is carried out through the use of a chemiluminescence detector. In addition, hybridization of RNA nucleic acid probes and *Giardia lamblia*-specific sequences can be detected by amplification using the MidiVariant (MDV)

plasmid and the RNA polymerase, QB replicase. Generation of a relatively large mass of recombinant RNA would serve as a signal that hybridization had occurred. (Lizardi, P. M., et al., *Biotechnology*, 6: 1196–1202 (1988)

In the present method, tailed capture probes are allowed to hybridize with target nucleotide sequences present in a sample, forming a capture probe/target nucleotide sequence complex. Either along with the capture probe or after the capture probe/target nucleotide sequence complex is formed, abelled detector probes are also contacted with the sample, which is maintained under appropriate conditions (e.g., of time, temperature, pH, salt concentration, chaotrope concentration) for hybridization of complementary nucleotide sequences to occur and for formation of a capture probe/target nucleotide sequence/detector probe complex. The capture probes and detector probes that are used bind to different regions of the target nucleotide sequence. The capture probe/target nucleotide sequence/detector probe complex, referred to as the hybridization complex, is removed from the sample mixture. This recovery is carried out, for example, by contacting the mixture containing hybridization complexes with a solid substrate which is coated with a polynucleotide complementary to the tail of the capture probe. The tail of the capture probe present in the hybridization complex hybridizes with the complementary substrate, making it possible to separate the entire hybridization complex from the sample. In the case of prehybridized capture probes or target nucleotide sequences, the substrate to which the capture probes or target nucleotide sequences are attached is removed from the sample mixture. Intact hybridization complexes may be released from the solid substrate by treatments which reversibly disrupt base pairings and complexes may be recaptured onto other solid substrates; the result of this cycling of hybridization complexes is reduction of noise which usually binds non-specifically to the solid substrate.

In another embodiment of this invention, only one type of probe is required, the labelled detector probes. In this case, the sample of target nucleotide sequences is bound to a solid support, as described later. The bound sample is contacted with one or more labelled detection probes in one or more liquid preparation(s) to permit hybridization of the solid support bound target nucleotide sequences and the labelled detector probe(s). The solid support material is then analyzed by the appropriate detection method for the hybridization complexes of labelled detector probes to solid support bound target nucleotide sequences.

Probe sets which include two or more selected nucleic acid probes, each of which hybridizes to a different region of ribosomal RNA of *Giardia lamblia* or ribosomal DNA of *Giardia lamblia*, can also be included. The use of probe sets can provide greater sensitivity and specificity. Probe sets can be comprised of capture probes, detector probes or a combination of capture and detector probes. Each probe in a set must bind to a different region of ribosomal RNA.

The assay format used in carrying out the present method will determine the appropriate combination of salt, solvent, nucleic acid concentrations, volumes and temperature used. Such conditions can be determined empirically by one of ordinary skill in the art. For example, in the solid support format of a dot blot assay, which is described in Example III, the hybridization solution for the oligonucleotide probes described can be comprised of 0.9M NaCl, 0.12M Tris-HCl, pH 7.8, 6 mM EDTA, 0.1M $KPO_4$, 0.1% SDS, 0.1% pyrophosphate, 0.002% Ficoll, 0.02% bovine serum albumin (BSA), and 0.002% polyvinylpyrrolidine.

While the description of the invention has been made with reference to detecting ribosomal RNA, the probes described herein and probes complementary to those described herein are also useful for the detection of the genes (DNA) which specify the ribosomal RNA. Thus, the probes can be RNA or DNA. Such probes are to be deemed equivalents to the described probes and encompassed within the spirit and scope to the present invention.

Nucleic acid probes which are specific for ribosomal RNA or ribosomal DNA of *Giardia lamblia* (i.e., bind to *Giardia lamblia* ribosomal RNA or DNA, but not to nucleic acids present in non-*Giardia lamblia* organisms) have been constructed. Such probes can be used individually or in combination (i.e., as part of a probe set) in the present method. Probes which are particularly useful in the present method are oligonucleotide probes having a nucleotide sequence which is complementary to at least a portion of 18S ribosomal RNA or to at least a portion of 18S ribosomal DNA of *Giardia lamblia*. The nucleotide sequence of a probe useful in the present method need not be totally complementary to a target nucleotide sequence. It is necessary that such a probe 1) be sufficiently complementary that it hybridizes selectively to a target nucleotide sequence and 2) remains hybridized to the target nucleotide sequence under the assay conditions used. The following oligonucleotide probes are useful in the present method:

Probe 1446: 5'-GTGTCCGGCTAGCAGGGACCGC-CGCGGGGGGTGCAACC-3'
Probe 1448: 5'-GTCGGGCCCTCGGCGCGCCGCGAC-CGCGCCGACCGGGTGA-3'
Probe 1449: 5'-GGGCCGTCGCTGCGTCACGCT-GCTCGCCCGCGGGCGCCCGC-3'
Probe 1450: 5'-CAACGGGCCTGCCTGGAGCGCTC-CCGTTTCCTCGTGGCGG-3'
Probe 1672: 5'-CTCCGCGGCGGGGGCTGTGGGC-CCGCCTCGCTCGCGCG-3'
Probe 1673: 5'-TGCGCGACGTCTTGGCGGCGGGT-TGCCAGCGGTGTCCGGCTAGCAGG-3'
Probe 1674: 5'-GGCGCGCCGCGCCCGCTGCGCGGTC-CCACGCGGCGGGTCCAACGGGCC-3'

Probes useful in the present method can be obtained from naturally-occuring sources, can be made using genetic engineering techniques or can be synthesized chemically.

The method of the present invention can be carried out in such a manner that hybridization occurs in an aqueous environment or on a solid support. When an aqueous environment is used, the treated sample, suspected to contain *Giardia lamblia*, is present in a liquid preparation, such as a physiological salt solution. The nucleic acid probes are also present in a liquid preparation. The two preparations are mixed together, which permits contact between target nucleotide sequences, if present, and the selected nucleic acid probes. If target nucleotide sequences are present, hybridization with the selected nucleic acid probes occurs. The sample can be combined with more than one type of selected nucleic acid probe, such as a set of probes in which each probe type hybridizes to a different location on the target nucleotide sequence.

In the embodiment of the present invention in which hybridization occurs on a solid support, either the target nucleotide sequences or the nucleic acid probes can be bound to the solid support. When target nucleotide sequences are bound to the solid support, the solid support is brought into contact with a selected nucleic acid probe(s), thus, making it possible for hybridization of the target nucleotide sequences and the selected nucleic acid probe(s) to occur. Conversely, when nucleic acid probes are bound to the solid support, the solid support is brought into contact with a sample suspected to contain the target nucleotide sequences, making it possible for hybridization of target nucleotide sequences with selected nucleic acid probes to occur.

Solid supports which can be used in the present invention include any solid material to which can be bound sufficient amounts of a substratum polynucleotide to allow a capture probe, as described above, or target nucleotide sequences to be prehybridized to the support. Polymeric materials, such as agarose beads or polystyrene, are generally useful as supports. Nitrocellulose and nylon filters can also be used. The configuration of the support will vary depending upon the type of assay and the nature of the samples to be assayed. Configurations such as microtiter wells, fibers and dipsticks are useful in the present invention and allow the simultaneous assay of a large number of samples to be performed manually in an efficient and convenient way. The assay can also be automated using, for example, automatic pipettes and plate readers. Other solid supports, particularly other plastic solid supports, can also be used.

When a solid support is used, a prehybridization solution containing protein and nucleic acid blocking agents is added to minimize "non-specific probe adhesion" to the solid support. By "non-specific probe adhesion" is meant the target-independent binding of a probe to a solid support. The force responsible for the sticking are not well understood (hence the use of the word "non-specific"), but van der Waals interactions, hydrophobic bonds, and hydrogen bonds are thought to be likely contributors to the total energy of the binding.

The means by which hybridization of complementary nucleic acid sequences is detected will be determined by the type of labelled probe used. For example, when radioactive ligands are used, the detection instrument can be a scintillation counter, densiotometer (for scanning autoradiographs) or a beta emission counter. If the detector label is fluorescein, the detection instrument can be a fluorescence spectrophotometer. In the case in which an enzyme is the detector probe label, the assay sample is pre-incubated with an appropriate chromagen/substrate before being read by a spectrophotometer at an appropriate wavelength.

The analysis of data involved in determining the presence or absence of *Giardia lamblia* using the nucleic acid probes described herein depends on the assay format and the type of label used for the nucleic acid probe. For example, in one embodiment using the dot blot format of Example III and a radioactive label for detection, positive samples representing the detection of the presence of ribosomal RNA or ribosomal DNA of *Giardia lamblia* are determined by taking the average counts per minute of three negative controls and adding 500 counts per minute to that average. This value represents the cutoff figure. The 500 counts per minute is added to the average to guard against standard variations in the value for negative controls. Samples with counts above the resultant cutoff figure are considered positive for *Giardia lamblia*. Samples with counts per minute less than the cutoff figure are considered negative.

A kit useful in carrying out the present method of detecting *Giardia lamblia* can be produced. Such a kit can include, for example, a sample processing solution containing a chelating agent, such as EDTA, and an agent (e.g., a chaotropic agent and/or a detergent such as sodium dodecyl sulfate) for disrupting molecular structures (e.g., membranes) of cells; tailed capture probes;labelled detector probes; at least one buffer; an agent for inhibiting RNAse enzymes (to prevent degradation of the target transcripts); a solid support (e.g., magnetic beads or polystyrene substrate) coated with a polynucleotide which is complementary to the capture probe tail; reference or standard nucleic acids to be run simultaneously with the sample as a control; and a wash buffer containing a detergent. The kit can optionally contain additional wash buffers, a means for detecting the labelled detector probe, one or more elution buffers, amplification or cloning reagents and/or additional positive control samples or negative control samples.

The assay steps of the present method can be automated. If microtiter plates are the solid support used, automatic pipetting equipment (for reagent addition and washing steps) and spectrophotometer readers can be used. An automated device for carrying out the present invention can include a pipetting station which can perform sequential operations of adding and removing reagents to the solid phase at specific time points in a thermostatted environment (i.e., temperature controlled environment) and a detection apparatus. The sequential operations include one or more of the following: mixing or contacting samples, lysis solutions and solid support; withdrawing fluid from the supports; adding wash buffer; repeating the steps enumerated above, adding labelled probes, repeating the wash steps again, adding detection agents, and detecting the signal with the detection instrument.

The invention is further illustrated by the following specific examples, which are not intended to be limiting in any way.

EXAMPLE I

Design of Giardia Lamblia Specific Oligonucleotide Probes

Oligonucleotide probes, 38 to 48 nucleotides in length, which hybridize selectively to *Giardia lamblia* have been produced. These were designed: 1) to utilize the nucleotide sequence differences between *Giardia lamblia* and other parasites and bacteria for distinguishing *Giardia lamblia* from non-*Giardia lamblia* organisms and 2) to minimize the effect of self-complementarity, both within the target ribosomal RNA and between probe molecules.

The first step taken in the design and development of the probes of the present invention involved identification of regions of 18S ribosomal RNA which could serve as target sites for *Giardia lamblia*-specific nucleic acid probes. Specifically, it was hypothesized that the exclusivity criteria could be satisfied by determining that if it were possible to identify a region(s) in *Giardia lamblia* ribosomal RNA which was sufficiently different from region(s) in the ribosomal RNA of close evolutionary relatives of *Giardia lamblia*, then a probe to such a sequence could be used to distinguish between *Giardia lamblia* and related organisms by hybridization assay. Based on phylogenetic observations, it then was extrapolated that ribosomal RNA sequences of more distantly related organisms, even though their actual identity may not necessarily be known, should be predictably different in a particular region of sequence than the aforementioned close evolutionary relative of *Giardia lamblia*.

As the first step in identifying regions of *Giardia lamblia* ribosomal RNA which could potentially serve as useful target sites for nucleic acid hybridization probes, the *Giardia lamblia* 18S-like ribosomal RNA nucleotide sequence (Sogin, M. L., et al, *Science*, 243:75–77 (1989)) was compared to other available ribosomal RNA nucleotide sequences, particularly to those of protozoan parasites. Comparison of the 18S-like rRNA nucleotide sequences of *Giardia lamblia* and other available rRNA nucleotide sequences of protozoan parasites proved especially useful. Several regions of sequence were identified which appeared to be different between *Giardia lamblia* and non-*Giardia lamblia* organisms. The location of these regions within the 18S-like ribosomal RNA sequences are shown in FIG. 1.

The probes, designed as described above and their target sequences in the 18S- like ribosomal RNA of *Giardia lamblia* are shown in FIG. 1. The specific hybridization behaviors of the probes described above are closely related to the assay format in which they are employed. Depending upon the format used, the character of the nucleic acid probes may differ. This can be determined empirically by one of ordinary skill in the art. For example, the length of these particular nucleic acid probes was optimized for use in the dot blot assay. It is well known to one skilled in the art that optimal probe length will be a function of the stringency of the hybridization conditions chosen and hence the length of the instant probes may be altered in accordance therewith. Thus, the exact length of a particular probe will to a certain extent reflect its specific intended use. The "essence" of the probes described herein reside in the discovery and utilization of the *Giardia lamblia* specific sequences described above. In those embodiments in which a set of more than one nucleic acid probe is used, it is necessary that all probes behave in a compatible manner in any particular format in which they are both employed.

EXAMPLE II

General Assay Format Utilizing Radiolabelled Detection Probes

Two grams of stool are liquified in 10 ml of phosphate buffer saline by mechanical homogenization. The liquid stool is filtered in a specially designed vacuum filtration manifold that holds 28 filter cups. Bacteria and debris from the liquid stool are trapped on the filter. Sodium hydroxide solution is added to the filter cup to break open any cells present and to denature double stranded DNA into single stranded DNA which can undergo reaction with added probe. A neutralization solution is added, followed by a fixation solution, to irreversibly fix the target *Giardia lamblia* ribosomal RNA or genomic DNA to the membrane. The cups are then broken open and the filters placed in a 50 ml centrifuge tube. All subsequent steps took place in batch in this tube. A pre-hybridization solution containing protein and nucleic acid blocking agents is added to minimize probe adhesion to the filters in the next step. Phorphorus$^{32}$-labelled probe(s) is then added and allowed to hybridize to any Giardia target ribosomal RNA or ribosomal DNA on the filter. This hybridization reaction is carried out in a 60° C. waterbath for two hours. The supernatant is decanted and the filters washed, in batch, a total of six times. The filters are then counted, either in a scintillation counter or in a beta detector. One positive sample (heat-killed *Giardia lamblia*, supplied with the kit) and three negatives (heat-killed *E. coli*) are run as controls with every assay. Positives are determined by taking the average of the three negatives and adding a constant of 500 counts per minute to that average. Samples above the resultant cutoff are considered presumptively positive for *Giardia lamblia*. Samples with counts less than the cutoff value are considered negative. Positive controls average about 10,000 to 30,000 counts per minute, depending on the age of the labelled nucleic acid probe, and are used only to ensure that the assay is done properly. The limit of sensitivity of this method, is about $5 \times 10^6$ organisms.

EXAMPLE III

Dot Blot Analysis of Probe Hybridization Behavior

The sequence comparisons described herein suggested that the probes of the present invention should exhibit a variety of useful hybridization properties with respect to the specific detection of Giardia lamblia to the exclusion of other protozoan parasites and bacteria. However, only one Giardia lamblia sequence was inspected. It is possible that sequence variation might exist in other Giardia lamblia not inspected by sequence analysis. Such variation might reduce or eliminate hybridization by the prospective probes to some or many untested Giardia lamblia isolates.

Equally as important as the inclusivity behavior of the probes, is their exclusivity behavior, i.e., their reactivity toward non-Giardia protozoan parasites and bacteria. The number and types of non-Giardia strains which might be encountered in a potentially Giardia-containing test sample are extremely large. Therefore, the behavior of the probes toward representative Giardia lamblia and non-Giardia organisms was determined by hybridization analysis using a dot blot procedure.

Dot blot analysis, which is a well-known technique, involves immobilizing a nucleic acid or a population of nucleic acids on a filter, such as nitrocellulose, nylon, or other derivitized membranes which can be obtained commercially, specifically for this purpose. Either DNA or RNA can be immobilized on such a filter and subsequently can be probed or tested for hybridization under any of a variety of conditions (i.e., stringencies) with nucleic acid probes of interest. Under stringent conditions, probes whose nucleotide sequences have greater complementarity to the target sequence will exhibit a higher level of hybridization than probes containing less complementarity.

For the experiment in which the results are illustrated in Table 1, one tenth of a microgram of purified RNA from each of the indicated organisms was spotted on nitrocellulose filters. The oligonucleotide probes were end-labelled with radioactive phosphorus using standard procedures.

For the oligonucleotide probes described herein, hybridization to ribosomal RNA targets at 60° C. for 14 to 16 hours (in a hybridization solution containing 0.9M NaCl, 0.12M Tris-HCL, pH 7.8, 6 mM EDTA, 0.1M KPO-4, 0.1% SDS, 0.1 % pyrophosphate, 0.002% ficoll, 0.002% BSA and 0.002% polyvinylpyrrolidone), followed by three 15-minute post hybridization washes at 60° C. (in 0.03M NaCl, 0.004M Tris-HCL, pH 7.8, 0.2 mM EDTA, and 0.1% SDS) to remove unbound probes, would be sufficiently stringent to produce the levels of specificity demonstrated in Table 1.

Following hybridization and washing as described above, the hybridization filters were exposed to x-ray film and the intensity of the signal scored visually with respect to control spots containing known amounts of target material (RNA) as described above.

TABLE 1

| DOT BLOT HYBRIDIZATION OF 18S-LIKE rRNA-TARGETED PROBES | | | | | | | | |
|---|---|---|---|---|---|---|---|---|
| | | PROBE HYBRIDIZATION | | | | | | |
| Genus species | strain | 1446 | 1448 | 1449 | 1450 | 1672 | 1673 | 1674 |
| Giardia: Beaver isolate | | ++++ | ++++ | ++++ | ++++ | ++++ | ++++ | ++++ |
| Giardia: CDC ( human ) | | ++++ | ++++ | ++++ | ++++ | ++++ | ++++ | ++++ |
| Giardia: Meyer ( human | | ++++ | ++++ | ++++ | ++++ | ++++ | ++++ | ++++ |
| Giardia: P1 ( human ) | | ++++ | ++++ | ++++ | ++++ | ++++ | ++++ | ++++ |
| Giardia: Sheep isolate | | ++++ | ++++ | ++++ | ++++ | ++++ | ++++ | ++++ |
| Giardia: W ( human ) | | ++++ | ++++ | ++++ | ++++ | ++++ | ++++ | ++++ |
| Giardia: WB ( human ) | | ++++ | ++++ | ++++ | ++++ | ++++ | ++++ | ++++ |
| Acinetobacter clacoaceticus | GT0002 | − | − | − | − | − | − | − |
| Acinetobacter lwoffii | GT0004 | − | − | − | − | − | − | − |
| Acinetobacter sobria | GT0007 | − | − | − | − | − | − | − |
| Bacillus cereus | GT0008 | − | − | − | − | − | − | − |
| Bacteroides fragilis | ATCC29771 | − | − | − | − | − | − | − |
| Bacteroides melaninogenicus | GT0011 | − | − | − | − | − | − | − |
| Bacteroides thetaiotamicron | GT0527 | − | − | − | − | − | − | − |
| Bifidobacterium dentium | GT0012 | − | − | − | − | − | − | − |
| Candida albicans | ATCC36232 | − | − | − | − | − | − | − |
| Candida tropicalis | 750 | − | − | − | − | − | − | − |
| Citrobacter diversus | GT0030 | − | − | − | − | − | − | − |
| Corynebacterium gentalium | GT0045 | − | − | − | − | − | − | − |
| Citrobacter freundii | GT0687 | − | − | − | − | − | − | − |
| Camphylobacter jejunii | ATCC33560 | − | − | − | − | − | − | − |
| Chlamydia trachomatis | LGV | − | − | − | − | − | − | − |
| Clostridium perfringens | ATCC13124 | − | − | − | − | − | − | − |
| Enterobacter agglomerans | GT0683 | − | − | − | − | − | − | − |
| Enterobacter cloacae | GT0686 | − | − | − | − | − | − | − |
| Enterobacter sakazakii | GT0062 | − | − | − | − | − | − | − |
| Escherichia coli | 1665 | − | − | − | − | − | − | − |
| Escherichia hermanii | GT0232 | − | − | − | − | − | − | − |
| Escherichia vulneris | GT0233 | − | − | − | − | − | − | − |
| Flavobacterium meningosepticum | GT0237 | − | − | − | − | − | − | − |
| Fusobacterium necrophorum | GT0238 | − | − | − | − | − | − | − |
| Fusobacterium prausnitzii | ATCC27768 | − | − | − | − | − | − | − |
| Hafnia alvei | GT0241 | − | − | − | − | − | − | − |
| Hemophilus influenzae | GT0244 | − | − | − | − | − | − | − |
| Kingella dentrificans | GT0245 | − | − | − | − | − | − | − |
| Kingella indologenes | GT0246 | − | − | − | − | − | − | − |
| Kingella kingae | GT0247 | − | − | − | − | − | − | − |
| Klesiella oxytoca | GT41 | − | − | − | − | − | − | − |
| Klebsella pneumonia | 1500 | − | − | − | − | − | − | − |
| Lactobacillus acidophilus | GT0256 | − | − | − | − | − | − | − |

TABLE 1-continued

DOT BLOT HYBRIDIZATION OF 18S-LIKE rRNA-TARGETED PROBES

| Genus species | strain | PROBE HYBRIDIZATION | | | | | | |
|---|---|---|---|---|---|---|---|---|
| | | 1446 | 1448 | 1449 | 1450 | 1672 | 1673 | 1674 |
| Lactobacillus casei | GT0805 | − | − | − | − | − | − | − |
| Lactobacillus minitus | GT0257 | − | − | − | − | − | − | − |
| Lactobacillus plantarum | GT0258 | − | − | − | − | − | − | − |
| Listeria welshmimeri | GT3170 | + | − | − | − | − | − | − |
| Listeria innocua | GT3171 | + | − | − | − | − | − | − |
| Listeria grayii | GT3174 | + | − | − | − | − | − | − |
| Listeria ivanovii | GT3342 | + | − | − | − | − | − | − |
| Listeria monocytogenes | GT3194 | + | − | − | − | − | − | − |
| Listeria monocytogenes | GT3299 | + | − | − | − | − | − | − |
| Listeria manocytogenes | GT3191 | + | − | − | − | − | − | − |
| Listeria monocytogenes | GT3344 | + | − | − | − | − | − | − |
| Listeria monocytogenes | GT3395 | + | − | − | − | − | − | − |
| Listeria seelegerii | | + | − | − | − | − | − | − |
| Morganella mogranii | IG3108 | − | − | − | − | − | − | − |
| Moraxella osloensis | GT0301 | − | − | − | − | − | − | − |
| Neisseria cinerea | GT0307 | − | − | − | − | − | − | − |
| Neisseria flavescens | GT0310 | − | − | − | − | − | − | − |
| Neisseria gonorrhoea | ATCC19424 | − | − | − | − | − | − | − |
| Neisseria meningitidis | GT0349 | − | − | − | − | − | − | − |
| Neisseria mucosa | GT0353 | − | − | − | − | − | − | − |
| Peptostreptococcus anaerobius | GT0359 | − | − | − | − | − | − | − |
| Plesiomonas shigelliodes | ATCC14029 | − | − | − | − | − | − | − |
| Proteus mirabilis | 1496 | − | − | − | − | − | − | − |
| Proteus vulgaris | GT0368 | − | − | − | − | − | − | − |
| Providencia alcalificiens | GT0371 | − | − | − | − | − | − | − |
| Providencia rettgeri | GT0373 | − | − | − | − | − | − | − |
| Providencia stuartii | GT0375 | − | − | − | − | − | − | − |
| Pseudomonas adidovorans | GT0376 | − | − | − | − | − | − | − |
| Pseudomonas aeruginosa | 1908 | − | − | − | − | − | − | − |
| Salmonella arizona | GT0799 | − | − | − | − | − | − | − |
| Salmonella typhimurium | GT0389 | − | − | − | − | − | − | − |
| Serratia marcescens | GT0392 | − | − | − | − | − | − | − |
| Shegella boydii C-13 | RF 974 | − | − | − | − | − | − | − |
| Shegella dysenteriae | RF 970 | − | − | − | − | − | − | − |
| Shegella flexnerii | GT0798 | − | − | − | − | − | − | − |
| Shegelia sonnei | RF 968 | − | − | − | − | − | − | − |
| Staphylococcus aureus | GT0399 | − | − | − | − | − | − | − |
| Staphylococcus epidermitis | GT0401 | − | − | − | − | − | − | − |
| Staphylococcus sanguis | GT0411 | − | − | − | − | − | − | − |
| Streptococcus agalactiae | GT0405 | − | − | − | − | − | − | − |
| Streptococcus faecalis | GT0406 | − | − | − | − | − | − | − |
| Streptococcus faecium | GT0407 | − | − | − | − | − | − | − |
| Streptococcus mutans | GT0412 | − | − | − | − | − | − | − |
| Streptococcus salivarius | GT0410 | − | − | − | − | − | − | − |
| Torlopsis globrata | ATCC2001 | − | − | − | − | − | − | − |
| Vibrio parahemolyticus | GT0568 | − | − | − | − | − | − | − |
| Xanthomonas maltophilia | GT0417 | − | − | − | − | − | − | − |
| Yersinia enterocolitica | GT0419 | − | − | − | − | − | − | − |
| McCoy cell RNA | | − | − | − | − | − | − | − |
| Human RNA from Whole Blood | | − | − | − | − | − | − | − |
| Human Stool RNA | | − | − | − | − | − | − | − |

*Inclusivity and Excluisivity data was determined after Overnight exposures.
**Each organism is represented by 100 ng of CsTFA purified RNA.
++++ = positive control level of hybridization, + = barely detectable and − = zero.

EXAMPLE IV

Probe Hybridization Behavior in Liquid-hybridization Assay

The probes of the present invention or derivatives thereof can be used in a variety of hybridization formats. One such format, a dual probe, sandwich- type hybridization assay formats (e.g., the homopolymer capture, dual probe, liquid hybridization format described in U.S. Ser. No. 277,579: 169,646, or U.S. Ser. No. 233,683), is used in this example. In general, in such an application, an oligonucleotide probe is modified at its 3' terminus to contain a track of deoxidenosine (dA) residues approximately 20–200 residues long. This is used to capture the target ribosomal RNA, following liquid hybridization, from the test sample onto a solid support (e.g., beads, plastic surface, filter, etc.) which had been suitably derivatized with poly-deoxythimidine (dT) for this purpose. A second probe is used as a detection probe and is derivatized by some detectable ligand (e.g., phosphorus$^{32}$, fluorescene, biotin, etc.). In principle, the detection probe can be a DNA or RNA probe with different lengths. Detection of the presence of the target nucleic acid in a test sample then is indicated by the capture of the detection ligand onto the solid surface through the series of hybridization interactions as illustrated in FIG. 2. This could occur only if the target nucleic acid is present in the sample. In principle, the above scheme could be employed with multiple-capture and detection probes (probe sets) for the purpose of, for example, improving or enhancing sensitivity of the assay.

Equivalents

Those skilled in the art will recognize, or be able to ascertain using no more than routine experimentation, many equivalents to the specific embodiment of the invention described specifically herein. Such equivalents are intended to be encompassed in the scope of the following claims.

We claim:

1. An isolated nucleic acid probe which hybridizes specifically to a target region of the 18S rRNA of *Giardia lamblia* when incubated with the target region at a temperature of 60° C. for 14–16 hours in a hybridization solution comprising 0.9M NaCl, 0.12M Tris-HCl (pH 7.8), 6 mM EDTA, 0.1M $KPO_4$, 0.1% SDS, 0.1% pyrophosphate, 0.002% ficoll, 0.002% BSA and 0.002% polyvinylpyrrolidone, followed by three 15 minute posthybridization washes at 60° C. in 0.03M NaCl, 0.004M Tris-HCl (pH 7.8), 0.2 mM EDTA, and 0.1% SDS, and which does not hybridize specifically to rRNA of non-*Giardia lamblia* under otherwise identical hybridization conditions, the target region being selected from the group consisting of:
5'-UCACCCGGUCGGCGCGGUCGCGGCGCGC-CGAGGGCCCGAC-3',
5'-GCGGGCGCCCGCGGGCGAG-CAGCGUGACGCAGCGACGGCCC-3',
5'-CCGCCACGAGGAAACGGGAGCGCUCCAG-GCAGGCCCGUUG-3',
5'-CGCGCGAGCGAGGCGGGCCCACAGC-CCCCGCCGCGG-3',
5'-CCUGCUAGCCGGACACCGCUGGCAAC-CCGGCGCCAAGACGUGCGCGCA-3' and
5'-GGCCCGUUGGACCCGCCGCGUGGGAC-CGCGCAGCGGGCGCGGCGCGCC-3'.

2. A nucleic acid probe of claim 1 consisting of the nucleic acid probe 5'-GTCGGGCCCTCGGCGCGCCGCGAC-CGCGCCGACCGGGTGA-3'.

3. A nucleic acid probe of claim 1 consisting of the nucleic acid probe 5'-GGGCCGTCGCTGCGTCACGCT-GCTCGCCCGCGGGCGCCCGC-3'.

4. A nucleic acid probe of claim 1 consisting of the nucleic acid probe 5'-CAACGGGCCTGCCTGGAGCGCTC-CCGTTTCCTCGTGGCGG-3'.

5. A nucleic acid probe of claim 1 consisting of the nucleic acid probe 5'-CTCCGCGGCGGGGGCTGTGGGCCCGC-CTCGCTCGCGCG-3'.

6. A nucleic acid probe of claim 1 consisting of the nucleic acid probe 5'-TGCGCGACGTCTTGGCGGCGGGTTGC-CAGCGGTGTCCGGCTAGCAGG-3'.

7. A nucleic acid probe of claim 1 consisting of the nucleic acid probe 5'-GGCGCGCCGCGCCCGCTGCGCGGTC-CCACGCGGCGGGTCCAACGGGCC-3'.

8. A method for detecting the presence of a target region of the 18S rRNA of *Giardia lamblia* in a sample, the method comprising:

a) providing a sample to be analyzed for the presence the target region of the 18S rRNA treated, if necessary, to render nucleic acids present in the sample available for hybridization with complementary sequences;

b) contacting the sample with an isolated nucleic acid probe which hybridizes specifically to a target region of the 18S rRNA of *Giardia lamblia* under the hybridization conditions defined in step c), and which does not hybridize specifically to rRNA of non-*Giardia lamblia* under otherwise identical hybridization conditions, the target region being selected from the group consisting of:
5'-UCACCCGGUCGGCGCGGUCGCGGCGCGC-CGAGGGCCCGAC-3',
5'-GCGGGCGCCCGCGGGCGAG-CAGCGUGACGCAGCGACGGCCC-3',
5'-CCGCCACGAGGAAACGGGAGCGCUCCAG-GCAGGCCCGUUG-3',
5'-CGCGCGAGCGAGGCGGGCCCACAGC-CCCCGCCGCGG-3',
5'-CCUGCUAGCCGGACACCGCUGGCAAC-CCGGCGCCAAGACGUGCGCGCA-3' and
5'-GGCCCGUUGGACCCGCCGCGUGGGAC-CGCGCAGCGGGCGCGGCGCGCC-3';

c) intubating the mixture of step b) at a temperature of 60° C. for 14–16 hours in a hybridization solution comprising 0.9M NaCl, 0.12M Tris-HCl (pH 7.8), 6 mM EDTA, 0.1M $KPO_4$, 0.1% SDS, 0.1% pyrophosphate, 0.002% ficoll, 0.002% BSA and 0.002% polyvinylpyrrolidone, followed by three 15 minute post-hybridization washes at 60° C. in 0.03M NaCl, 0.004M Tris-HCl (pH 7.8), 0.2 mM EDTA, and 0.1% SDS; and d) detecting specific hybridization as an indication of the presence of a target region of the 18S rRNA of *Giardia lamblia* in a sample.

9. A method of claim 8 wherein the nucleic acid probe is 5'-GTCGGGCCCTCGGCGCGCCGCGAC-CGCGCCGACCGGGTGA-3'.

10. A method of claim 8 wherein the nucleic acid probe is 5'-GGGCCGTCGCTGCGTCACGCTGCTCGC-CCGCGGGCGCCCGC-3'.

11. A method of claim 8 wherein the nucleic acid probe is 540 -CAACGGGCCTGCCTGGAGCGCTC-CCGTTTCCTCGTGGCGG-3'.

12. A method of claim 8 wherein the nucleic acid probe is 5'-CTCCGCGGCGGGGGCTGTGGGCCCGC-CTCGCTCGCGCG-3'.

13. A method of claim 8 wherein the nucleic acid probe is 5'-TGCGCGACGTCTTGGCGGCGGGTTGC-CAGCGGTGTCCGGCTAGCAGG-3'.

14. A method of claim 8 wherein the nucleic acid probe is 5'-GGCGCGCCGCGCCCGCTGCGCGGTC-CCACGCGGCGGGTCCAACGGGCC-3'.

\* \* \* \* \*